United States Patent [19]

Kishita et al.

[11] Patent Number: 5,262,557

[45] Date of Patent: Nov. 16, 1993

[54] FLUORINE-CONTAINING ORGANOSILICON COMPOUND AND PROCESS FOR PRODUCING THE SAME

[75] Inventors: Hirofumi Kishita, Annaka; Kouichi Yamaguchi; Shuji Suganuma, both of Takasaki, all of Japan

[73] Assignee: Shin-Etsu Chemical Co., Ltd., Tokyo, Japan

[21] Appl. No.: 961,829

[22] Filed: Oct. 16, 1992

[30] Foreign Application Priority Data

Oct. 17, 1991 [JP] Japan .................. 3-298321

[51] Int. Cl.$^5$ ............................................. C07F 7/08
[52] U.S. Cl. ............................................. 556/448
[58] Field of Search .................................. 556/448

[56] References Cited

U.S. PATENT DOCUMENTS

| | | | |
|---|---|---|---|
| 4,968,828 | 11/1990 | Yamamoto | 556/448 |
| 4,996,344 | 2/1991 | Inomata et al. | 556/448 |
| 5,043,464 | 8/1991 | Yamamoto | 556/448 X |
| 5,099,053 | 3/1992 | Takaoka et al. | 556/448 |
| 5,124,467 | 6/1992 | Rodgers et al. | 556/448 X |

FOREIGN PATENT DOCUMENTS

| | | | |
|---|---|---|---|
| 0328397 | 8/1989 | European Pat. Off. | 556/448 |
| 0414186 | 2/1991 | European Pat. Off. | 556/448 |
| 0418568 | 3/1991 | European Pat. Off. | 556/448 |
| 3830572 | 3/1989 | Fed. Rep. of Germany | 556/448 |
| 2311485 | 12/1990 | Japan | 556/448 |

*Primary Examiner*—Paul F. Shaver
*Attorney, Agent, or Firm*—Oblon, Spivak, McClelland, Maier & Neustadt

[57] ABSTRACT

A fluorine containing organosilicon compound represented by the following general formula:

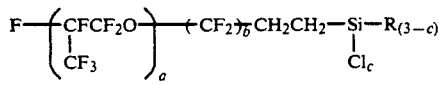

wherein R represents an alkyl group or an aryl group, a is an integer of 1 to 7, b is an integer of 2 to 8, and c is an integer of 1 to 3. This compound is useful as a surface treating agent for silicas, an adhesive improver for resists, an oil or water-repellent treating agent, and a raw material for synthesis of various silicone compounds.

4 Claims, 2 Drawing Sheets

FLUORINE-CONTAINING ORGANOSILICON COMPOUND AND PROCESS FOR PRODUCING THE SAME

BACKGROUND OF THE INVENTION

1. Field of the Invention

The present invention relates to a novel organosilicon compound useful, for example, as an intermediate for synthesis of various silicone compounds and a process of producing the same.

2. Description of the Prior Art

Fluorine-containing organosilicon compounds are generally excellent in properties such as heat resistance, chemical resistance, and weather resistance and are conventionally used, for example, as raw materials for production of various silicone oils and silicone elastomers.

Conventionally known fluorine-containing organosilicon compounds have structures wherein a fluorine-containing group such as a perfluoroalkyl group is bonded to a silicon atom directly or through a trimethylene group ($-CH_2CH_2CH_2-$).

SUMMARY OF THE INVENTION

An object of the present invention is to provide a novel and useful fluorine-containing organosilicon compound different from prior fluorine-containing organosilicon compounds and a process of producing the same.

According to the present invention, there is provided a fluorine-containing organosilicon compound represented by the following general formula (1):

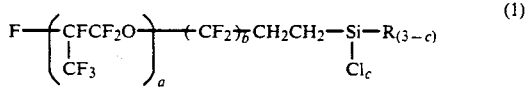  (1)

wherein R represents an alkyl group having 1 to 8 carbon atoms or an aryl group, if there are two R's, they may be the same or different, a is an integer of 1 to 7, b is an integer of 2 to 8, and c is an integer of 1 to 3.

Further, according to the present invention, there is also provided a process of producing a fluorine-containing organosilicon compound represented by the above general formula (1), comprising the step of reacting a chlorosilane represented by the following general formula (2):

  (2)

wherein R and c have the same meanings as defined above and a fluorine-containing olefin represented by the following general formula (3):

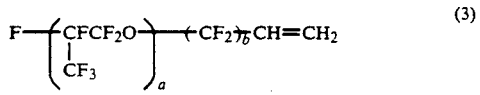  (3)

wherein a and b have the same meanings as defined above in the presence of a platinum family metal catalyst.

DETAILED DESCRIPTION OF THE INVENTION

Fluorine-containing organosilicon compounds

Figure 1:
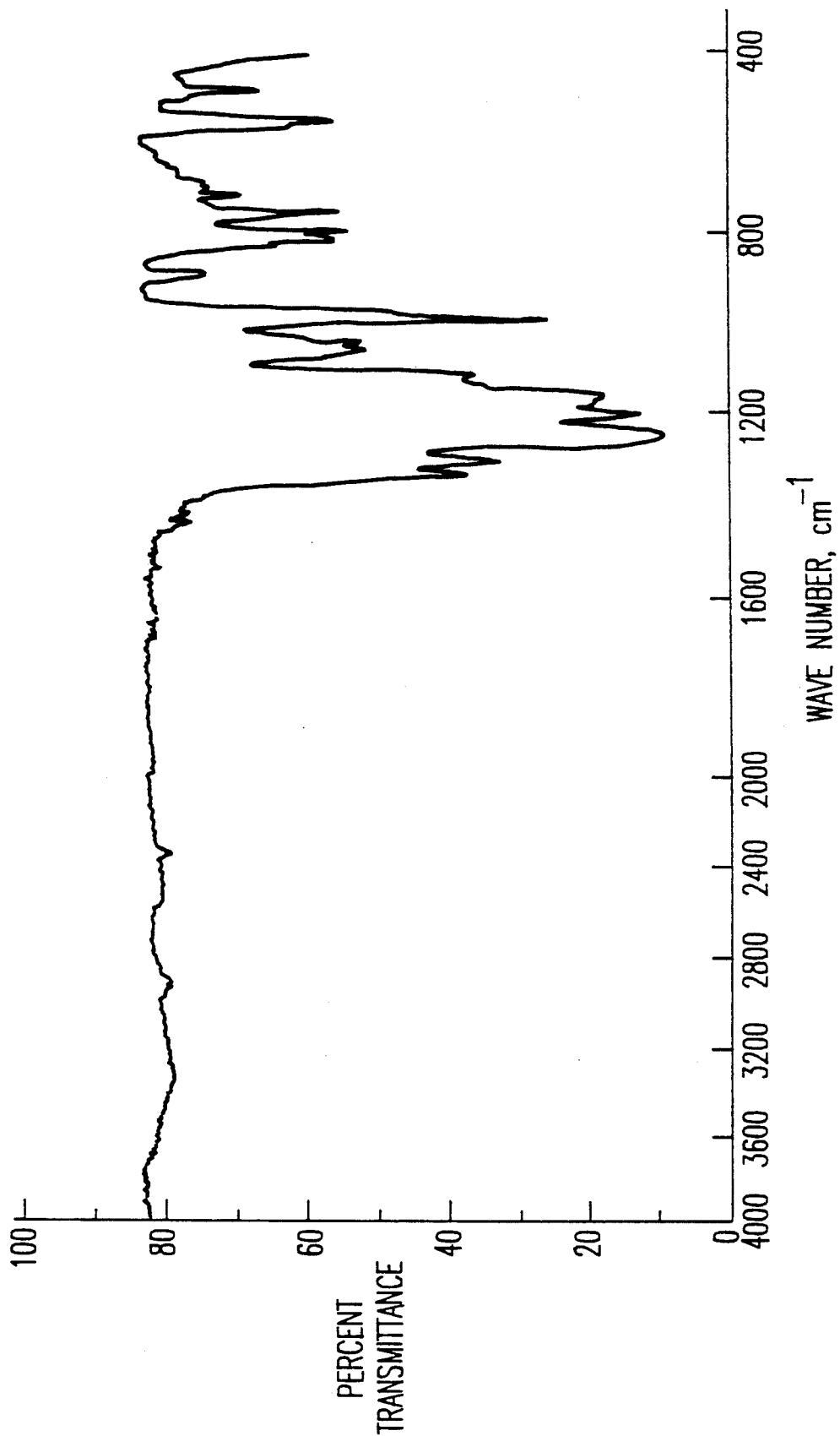
FIG. 1 is a diagram showing the IR spectrum of the compound synthesized in Example 1.

The fluorine-containing organosilicon compound of the present invention is represented by the above general formula (1).

In said formula, R is an alkyl group having 1 to 8 carbon atoms or an aryl group and examples include a methyl group, an ethyl group, a propyl group, a butyl group, a pentyl group, an octyl group, and a phenyl group. If there are two R's in the molecule, these R's may be the same or different. As defined above, a is an integer of 1 to 7, b is an integer of 2 to 8, and c is an integer of 1 to 3.

Typical examples of the fluorine-containing organosilicon compound include the following compounds:

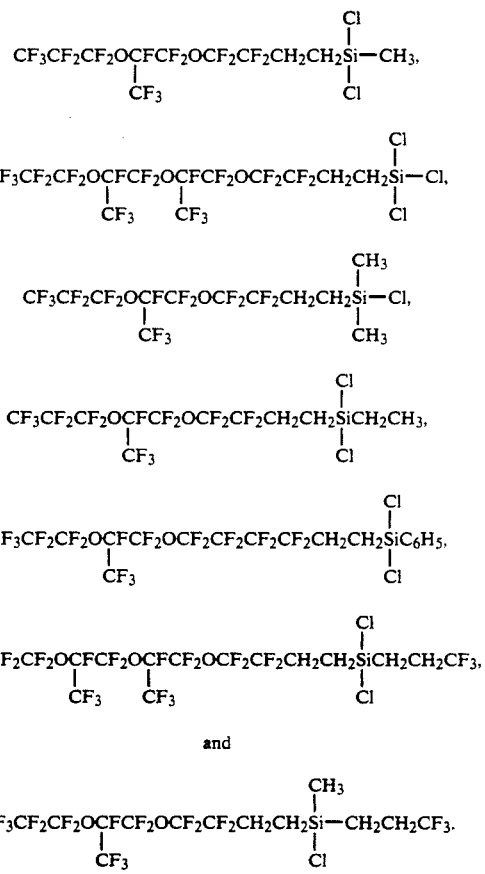

and

Since the present fluorine-containing organosilicon compound has an SiCl group, the reactivity is high.

Further, since the present fluorine-containing organosilicon compound has a fluorine-containing organic group comprising a perfluoroalkyl ether group(s), the present fluorine-containing organosilicon compound is excellent in properties such as heat resistance, chemical resistance, and weather resistance, and by changing the size of the fluorine containing organic group, these properties can be exhibited in accordance with the intended application. Moreover, this fluorine-containing organic group is bonded through a dimethylene group (—CH$_2$CH$_2$-) to a silicon atom and this leads to an advantage that the compound is chemically stable in comparison with the case of the bond through a trimethylene group.

Therefore, the present fluorine-containing organosilicon compound are quite useful to be used, for example, as a raw material for synthesis of various silicone compounds; as a surface treating agent for silicas used as a filler to be blended with various organic resins, silicone oil compounds, silicone rubbers, etc.; as an adhesion improver used, for example, in resists in the production process of semiconductor devices; and as a surface treating agent for rendering the surface of optical lenses, lenses of glasses, glass implements, and the like oil and water repellent and stainproof.

Process of the Preparation

The present fluorine-containing organosilicon compound described above can be synthesized by reacting a chlorosilane represented by the above general formula (2) and a fluorine-containing olefin represented by the above general formula (3) in the presence of a platinum family metal catalyst.

In the above general formula (2), R and c have the same meanings as defined above and specific examples of the chlorosilane represented by the general formula (2) include the following, but the present invention is not restricted to them.

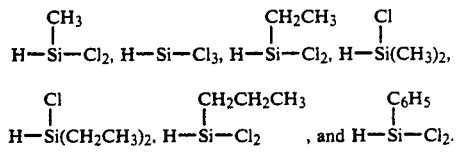

In the above general formula (3), a and b have the same meanings as defined above and specific examples of the fluorine-containing olefin represented by the general formula (3) include the following, but the present invention is not restricted to them.

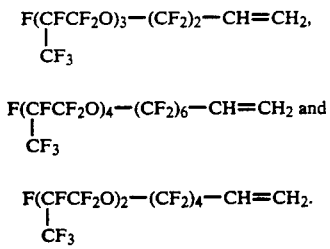

The reaction of the above chlorosilane and the above fluorine-containing olefin is the addition reaction of the SiH group in the chlorosilane and the unsaturated bond in the fluorine-containing olefin. In this reaction, the chlorosilane is preferably used in an amount of about 1 to 2 mol, particularly 1.1 to 1.3 mol, per mol of the fluorine. containing olefin.

The above platinum family metal catalyst used as a catalyst in the above reaction includes a platinum catalyst, a palladium catalyst, and a rhodium catalyst with preference given to a platinum catalyst and specific examples of the platinum catalyst include platinum black; a catalyst having solid platinum carried on a carrier such as alumina and silica; chloroplatinic acid; an alcohol-modified chloroplatinic acid; a complex of chloroplatinic acid with an olefin; and a complex of platinum with a vinyl siloxane.

The amount of these catalysts to be blended may be the catalytic amount and generally may be $1 \times 10^{-6}$ to $1 \times 10^{-3}$ mol per mol of the fluorine-containing olefin represented by the general formula (3). More specifically, for example, if a platinum catalyst is used, the amount is generally $1.0 \times 10^{-6}$ to $1.0 \times 10^{-4}$ in terms of platinum, preferably $1.0 \times 10^{-5}$ to $5.0 \times 10^{-5}$ mol in terms of platinum, per mol of the fluorine-containing olefin represented by the above general formula (3).

The above reaction can be carried out without any solvent or by using a suitable solvent.

Although the reaction temperature is adjusted in accordance with the kinds of the chlorosilane, the fluorine-containing olefin, and the catalyst that are used, generally the reaction temperature is in the range of 50° to 150° C., particularly preferably 100° to 120° C., and the reaction time is generally about 5 to 100 hours, particularly about 10 to 70 hours.

After the completion of the reaction, purification, for example, by distillation under reduced pressure is carried out in conventional manner to obtain the intended fluorine. containing organosilicon compound.

The olefin represented by the general formula (3) used in the above synthesis is obtained, for example, by the known method shown below.

That is, an alkali metal fluoride such as cesium fluoride and potassium fluoride is dissolved in an aprotic organic solvent such as diglyme and tetraglyme, and hexafluoropropylene oxide (HFPO) is blown into the obtained solution at a low temperature to oligomerize the HFPO to synthesize an HFPO oligomer acid fluoride represented by the following general formula (4):

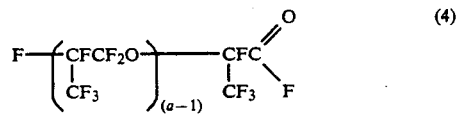

wherein a has the same meaning as defined above.

This HFPO oligomer acid fluoride is reacted with tetrafluoroethylene and iodine in an aprotic organic solvent in the presence of an alkali metal fluoride (an iodine etherification reaction) to obtain a perfluoroether iodide. This reaction is represented by the expression shown below and is generally carried out in an autoclave.

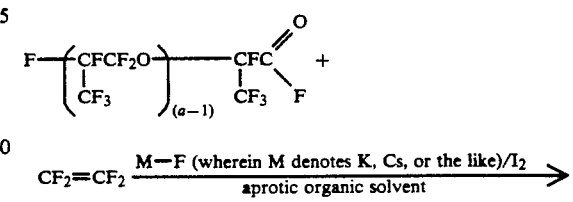

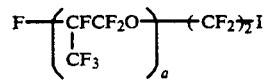

wherein a has the same meaning as defined above.

Ethylene is blown into the perfluoroether iodide obtained by the above reaction in the presence of a radical addition reaction catalyst such as azobisisobutyronitrile and a peroxide to carry out an ethylene addition reaction represented by the following reaction formula:

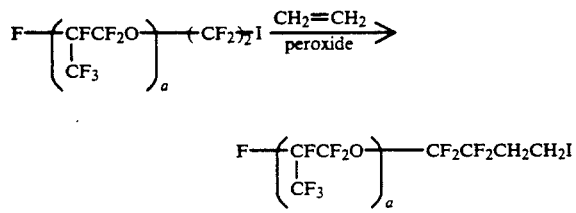

to produce a fluorine-containing alkyl ether ethyl iodide.

By adding dropwise the fluorine-containing alkyl ether ethyl iodide to an alkali metal hydroxide such as potassium hydroxide and sodium hydroxide in an alcohol solvent such as methanol, a fluorine-containing olefin represented by the above general formula (3) can be obtained.

EXAMPLES

Example 1

97 g of a fluorine-containing olefin represented by the following chemical formula (5):

$$CF_3CF_2CF_2OCFCF_2OCF_2CF_2CH=CH_2 \quad (5)$$
$$\phantom{CF_3CF_2CF_2OC}|$$
$$\phantom{CF_3CF_2CF_2OC}CF_3$$

and 28 g of dichloromethylsilane were placed in a 350-ml autoclave and 0.04 g of a platinum catalyst was also placed therein.

Then, the temperature inside the autoclave was brought to 120° C. and the reaction was carried out for 20 hours. After the completion of the reaction, the obtained reaction mixture was distilled and 79.5 g of a fraction having a boiling point of 81° C./10 mmHg was obtained (yield: 67%).

To identify the molecular structure of the obtained fraction, the elemental analysis was carried out and the IR spectrum and $^1$H-NMR spectrum were measured, thereby obtaining the following results:

| Elemental analysis: | C | H | Si | F |
|---|---|---|---|---|
| Calculated for $C_{11}H_7O_2F_{17}Cl_2Si_1$ | 22.27 | 1.19 | 4.74 | 54.45 |
| Found | 22.31 | 1.21 | 4.69 | 54.18 |

IR spectrum: shown in FIG. 1.
C-H: 2950 cm$^{-1}$
C-F: 1,100 to 1,340 cm$^{-1}$
$^1$H-NMR spectrum: in CCl$_4$; internal standard: CHCl$_3$ δ(ppm)
(s, j3H, Si-CH$_3$) 0.9
(m, 2H, Si-CH$_2$-C) 1.1 to 1.7
j(m, 2H, Si-C-CH$_2$-C) 2.2 to 2.8

From the above results, the obtained fraction was identified as an organosilicon compound represented by the following formula:

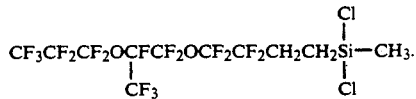

EXAMPLE 2

Example 1 was repeated, except that, in place of the fluorine-containing olefin represented by the chemical formula (5), 33 g of a fluorine-containing olefin represented by the following chemical formula (6):

$$CF_3CF_2CF_2OCFCF_2OCFCF_2OCF_2CF_2CH=CH_2 \quad (6)$$
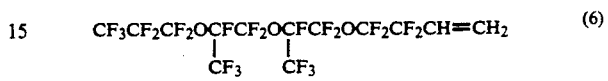

was used, 28 g of dichlorosilane was changed to 33 g of trichlorosilane, and the reaction time was changed to 31 hours, thereby obtaining a fraction having a boiling point of 132° C./35 mmHg (yield: 71%).

To identify the molecular structure of the obtained fraction, the elemental analysis was carried out and the IR spectrum and $^1$H-NMR spectrum were measured, thereby obtaining the following results:

| Elemental analysis: | C | H | Si | F |
|---|---|---|---|---|
| Calculated for $C_{13}H_4O_3F_{23}Cl_3Si_1$ | 18.40 | 0.47 | 3.30 | 51.53 |
| Found | 18.36 | 0.50 | 3.31 | 51.28 |

Figure 2:
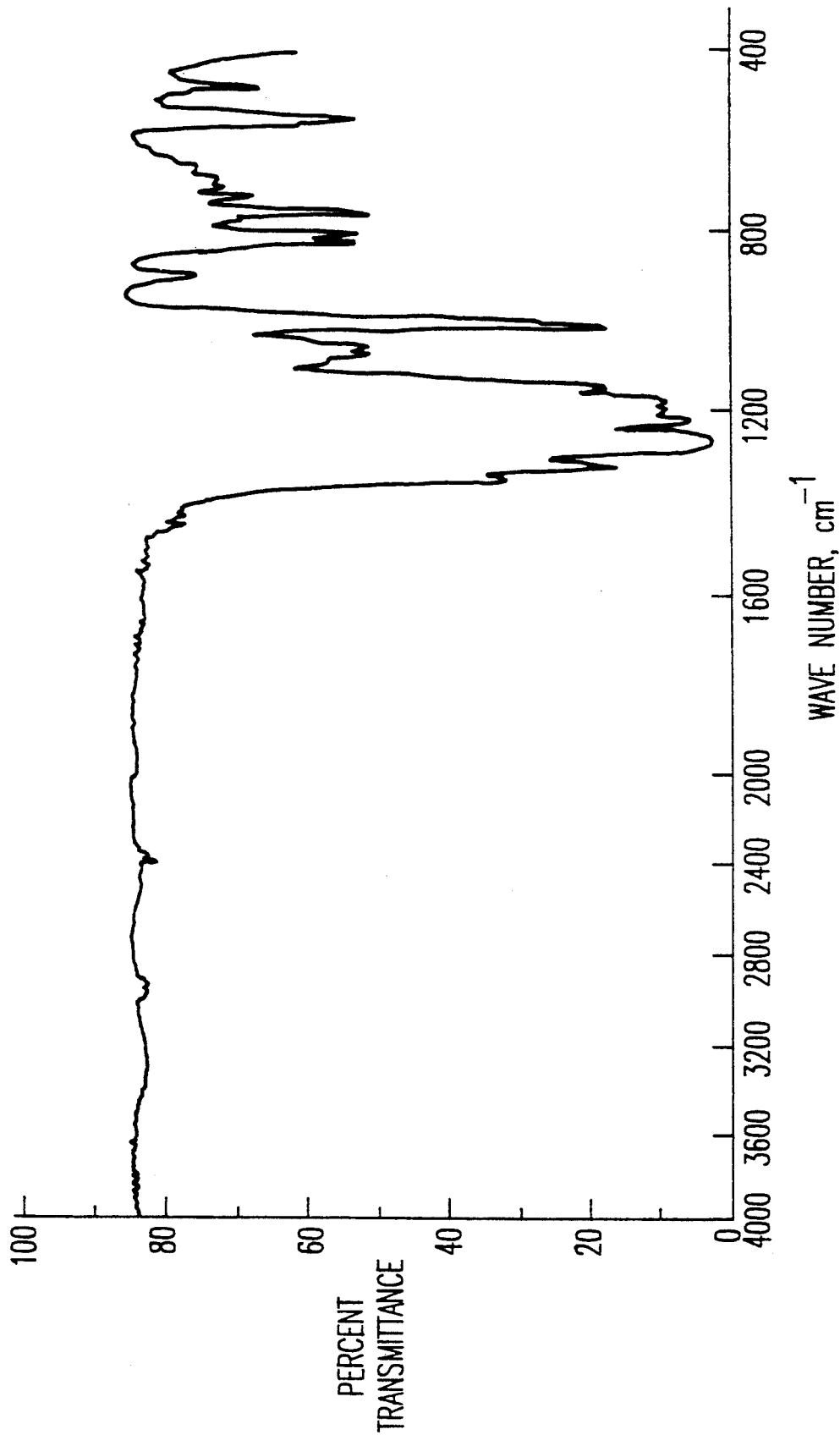
FIG. 2 is a diagram showing the IR spectrum of the compound synthesized in Example 2.

IR spectrum: shown in FIG. 2.
C-H: 2950 cm$^{-1}$
C-F: 1,100 to 1,340 cm$^{-1}$
$^1$H-NMR spectrum: in CCl$_4$; internal standard: CHCl$_3$ δ(ppm)
(m, 2H, Si-CH$_2$C) 1.4 to 1.9
(m, 2H, Si-C-CH$_2$-C) 2.1 to 2.7

From the above results, the obtained fraction was identified as an organosilicon compound represented by the following formula:

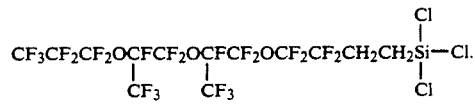

We claim:

1. A fluorine-containing organosilicon compound represented by the following general formula (1):

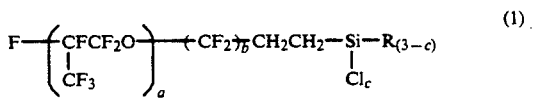

wherein R represents an alkyl group having 1 to 8 carbon atoms or an aryl group, if there are two R's, they may be the same or different, a is an integer of 1 to 7, b is an integer of 2 to 8, and c is an integer of 1 to 3.

2. A fluorine-containing organosilicon compound as claimed in claim 1, wherein in said general formula (1) c is 3.

3. A fluorine-containing organosilicon compound as claimed in claim 1, wherein in said general formula (1) c is 1 or 2, and R is a methyl group.

4. A process of producing a fluorine-containing organosilicon compound as claimed in claim 1, comprising the step of reacting a chlorosilane represented by the following general formula (2):

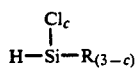 (2)

wherein R represents an alkyl group having 1 to 8 carbon atoms or an aryl group, if there are two R's, they may be the same of different, and c is an integer of 1 to 3 and a fluorine-containing olefin represented by the following general formula (3):

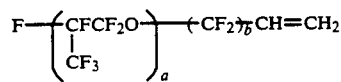 (3)

wherein a is an integer of 1 to 7 and b is an integer of 2 to 8 in the presence of a platinum family metal catalyst.

* * * * *